United States Patent [19]

Angel et al.

[11] 4,251,768

[45] Feb. 17, 1981

[54] COINCIDENCE CORRECTION OF HEMATOCRIT IN A HEMATOLOGY MEASUREMENT APPARATUS

[75] Inventors: Henry R. Angel; Bernard O. Bachenheimer, both of Fairfield, Conn.

[73] Assignee: Hycel, Inc., Houston, Tex.

[21] Appl. No.: 947,663

[22] Filed: Sep. 29, 1978

[51] Int. Cl.³ .............................................. G01N 27/00
[52] U.S. Cl. ............................. 324/71 CP; 235/92 PC
[58] Field of Search ............... 235/92 PC; 324/71 CP

[56] References Cited

U.S. PATENT DOCUMENTS

| | | | |
|---|---|---|---|
| 3,936,739 | 2/1976 | Hogg | 324/71 CP |
| 3,936,741 | 2/1976 | Cowlter | 324/71 CP |
| 3,987,391 | 10/1976 | Hogg | 324/71 CP |
| 4,042,808 | 8/1977 | Hennessy | 235/92 PC |

*Primary Examiner*—Michael J. Tokar
*Attorney, Agent, or Firm*—Robert P. Cogan; Tim L. Burgess

[57] ABSTRACT

In a hematology measurement apparatus, a hematocrit value is generated by incrementing a value in accumulation means in accordance with measured sizes of red blood cells. The hematocrit value is corrected for coincidence by incrementing the value additionally in response to the production of red blood cell count coincidence corrections pulses.

12 Claims, 4 Drawing Figures

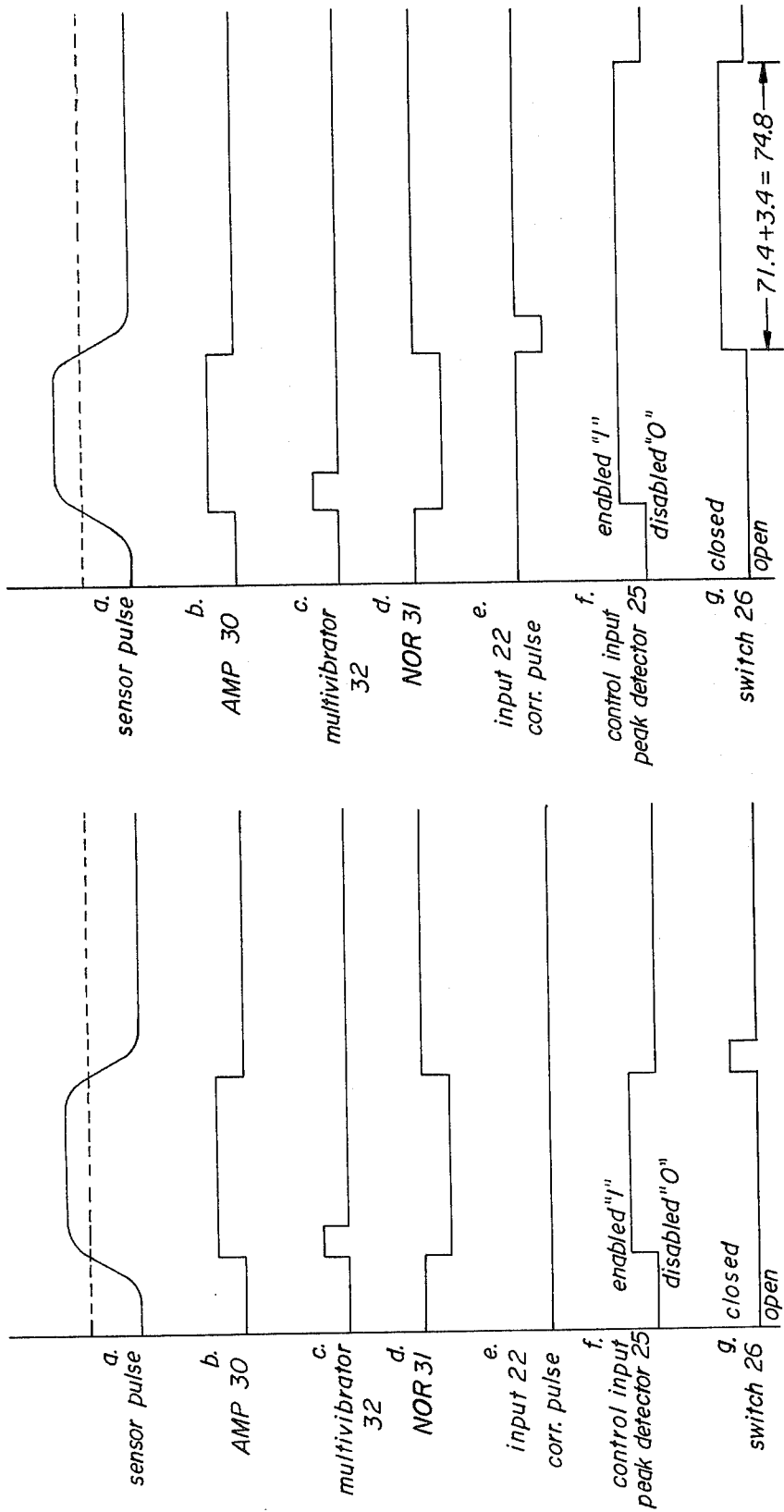

COINCIDENCE CORRECTION OF HEMATOCRIT IN A HEMATOLOGY MEASUREMENT APPARATUS

BACKGROUND OF THE INVENTION

The present invention relates to an apparatus and to a method for determining hematocrit, and more particularly to coincidence correction in such an apparatus and method.

Hematocrit is the percentage of packed red blood cells in a sample of whole blood. Hematocrit measurement is commonly performed within a blood cell counting instrument. Examples of hematocrit measurement apparatus and blood cell counting apparatus are found, for example, respectively in U.S. Pat. No. 4,068,169 issued Jan. 10, 1978 to Henry R. Angel and Bernard O. Bachenheimer and U.S. Pat. No. 3,921,066 issued Nov. 18, 1975 to Henry R. Angel and James W. Hennessy. Both patents have been assigned to the assignee herein, and their disclosures are incorporated herein by reference. Different forms of hematocrit measurement circuits in a hematology counter are well-known in the art. The above cited patent to Angel and Bachenheimer as well as U.S. Pat. No. 3,828,260 issued to Raymond D. Underwood on Aug. 6, 1974 disclose circuits in which the size of each pulse representing a red blood cell count is measured and signals each indicative of volume of a blood cell volume are totalized. This is referred to as direct measurement of hematocrit. Another form of hematocrit measurement apparatus is disclosed in U.S. Pat. No. 3,439,267 issued Aug. 15, 1969 to Wallace H. Coulter and Walter R. Hogg. Hematocrit is calculated as a function of mean corpuscular volume times the red blood cell count. This type of circuit is distinguished from the type in which cell volumes are totalized.

The red blood cell count has a coincidence correction factor applied thereto. Red blood cell count pulses are produced by impedance changes in an aperture resulting from blood cells passing therethrough. More than one cell may coincidentially pass through the aperture at one time, so a coincidence correction factor must be applied to a "raw" red blood cell count to provide an actual count. Many coincidence correction circuits are well-known in the art for use in producing red blood cell counts. It has long been known that applying a coincidence correction factor which is the function of the magnitude of a red blood cell count is desirable. However, coincidence correction has heretofore not been applied to direct measurement of hematocrit.

When a red blood cell is not counted due to coincidence, its size is not measured, and a pulse indicative thereof is not provided for incrementing accumulation means. The effect of coincidence error may not be highly significant when performing counts on samples in which the sample is blood highly diluted in saline diluent (e.g. 1:150,000) or in which the red blood cell count is low. Significance of the effect increases with density of the blood dilution or with level of red blood cell count. It has been discovered that coincidence correction has utility in direct measurement of hematocrit.

SUMMARY OF THE INVENTION

It is therefore an object of the present invention to provide in a hematology measurement apparatus a hematocrit measurement circuit and method which measures hematocrit directly and in which a coincidence correction factor is utilized to produce an output having a value indicative of hematocrit.

It is also an object of the present invention to provide in a hematology measurement apparatus in which a value in accumulation means is incremented in accordance with measured sizes of red blood cells, a method and apparatus for further incrementing the value in response to the production of coincidence correction pulses.

Briefly stated, in accordance with the present invention, there is provided in a hematology measurement apparatus, a method and apparatus in which a hematocrit value is generated by incrementing a value in accumulation means in accordance with measured sizes of red blood cells. The hematocrit value is corrected for coincidence by incrementing the value additionally in response to the production of red blood cell count coincidence corrections pulse.

BRIEF DESCRIPTION OF THE DRAWINGS

The means by which the foregoing objects and features of invention are achieved are pointed out with particularity in the claims forming the concluding portion of the specification. The invention, both as to its organization and manner of operation, may be further understood by reference to the following description taken in connection with the drawings.

Of the drawings:

FIGS. 3 and 4 are waveform charts useful in understanding the operation of the circuit of FIG. 2.

DESCRIPTION OF THE PREFERRED EMBODIMENT

Figure 1:
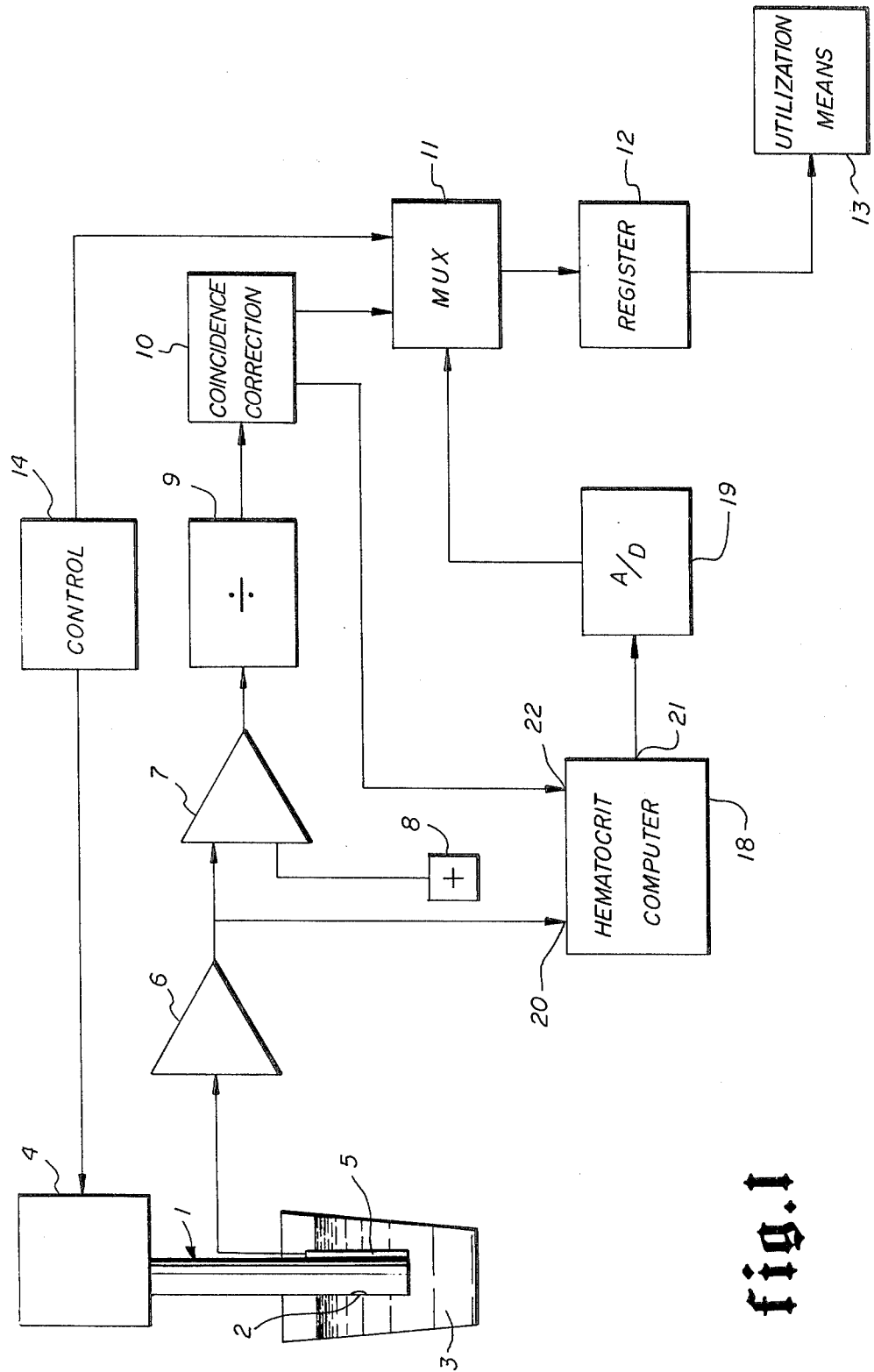
FIG. 1 is a block diagrammatic representation of a hematology measurement apparatus incorporating the present invention.

Referring to FIG. 1, there is illustrated an apparatus for performing red blood cell counts and measuring hematocrit. This apparatus may be constructed in accordance with the U.S. Pat. No. 3,921,066 to Angel et al cited above, and may be included in apparatus which measures, for example, the conventionally selected groups of three, five or seven hematology parameters. A well-known conductivity probe 1 having an aperture 2 is provided for counting blood cells in a sample 3. Well-known hydraulic means 4 aspirate liquid from the sample 3, comprising a dilution of blood in saline solution, into the probe 1 to produce pulses at an electrode 5 indicative of blood cells in the sample 3 in a well-known manner. The electrode 5 supplies pulses indicative of the sensing of blood cells, hereinafter called sensor pulses, to a buffer amplifier 6 having its output connected to provide input pulses for performing both red blood cell counts and hematocrit measurement.

Red blood cell counting is performed in a conventional manner by connecting the output of the buffer amplifier 6 to a threshold comparator 7, comprising an operational amplifier having a source 8 of threshold potential connected thereto as well. Pulses exceeding the threshold level are coupled from the threshold comparator 7 to a divider circuit 9 providing an input to a coincidence correction circuit 10 to correct the raw count for coincidence. Coincidence is a well-known phenomenon in which two or more blood cells may pass through the aperture 2 and provide a single sensor pulse at the output of the buffer amplifier 6 indicative of only one cell. Coincidence correction techniques in circuitry are well-known in the art. The coincidence correction circuit 10 may, for example, be constructed in accordance with now commonly assigned U.S. Pat. No. 4,042,808 issued Aug. 16, 1977 to James W. Hennessy, Henry R. Angel and Bernard O. Bachenheimer, the disclosure of which is incorporated herein by reference. Numerous other coincidence correction circuits are well-known in the art. The number of pulses provided at the output of the coincidence correction circuit 10 is indicative of the number of red blood cells per unit volume in the sample 3. The output of the coincidence correction circuit 10 is coupled by a multiplexer 11 to a register means 12, which is connected to supply a value to utilization means 13. The register means 12 comprises a well-known demultiplexer and a plurality of registers for performing the conventional function of translating outputs to the utilization means 13. The utilization means 13 may take one or more of many well-known forms such as, for example, a display, a printer, recorder or a computer memory. The multiplexer 11 is controlled by a conventional control circuit 14 which may include conventional function selection buttons and which also is coupled to control operation of the hydraulic means 4.

For purposes of operation as will be described with respect to FIG. 4 below, the coincidence correction circuit 10 should be of the type in which coincidence correction pulses that are produced each immediately follow a sensor pulse. The above cited U.S. Pat. No. 4,042,808 to Hennessy, Angel and Bachenheimer is a suitable circuit. A circuit in which groups of correction pulses are provided in one interval and not interleaved with sensor pulses, e.g. the circuit of U.S. Pat. No. 3,737,633 to Collineau, is not suitable.

To provide an output indicative of hematocrit, the buffer amplifier 6 is connected to a hematocrit computer 18 which is illustrated in schematic form. In the present embodiment, the hematocrit computer 18 generates an analog value indicative of hematocrit for the sample 3. The output of the hematocrit computer 18 is connected to an analog to digital converter 19 having an output connected to the multiplexer 11 so that a value can be supplied to the utilization means 13. Alternatively, the output of the analog to digital converter 19 may be supplied directly to a register or other well-known utilization means. In accordance with the present invention, and as more fully described hereinbelow, an input is provided to the hematocrit computer 18 from the coincidence correction circuit 10 to provide for coincidence correction of the hematocrit value generated. The hematocrit computer 18 has an input terminal 20 and output terminal 21 and a terminal 22 for receiving an input from the coincidence correction circuit 10.

Figure 2:
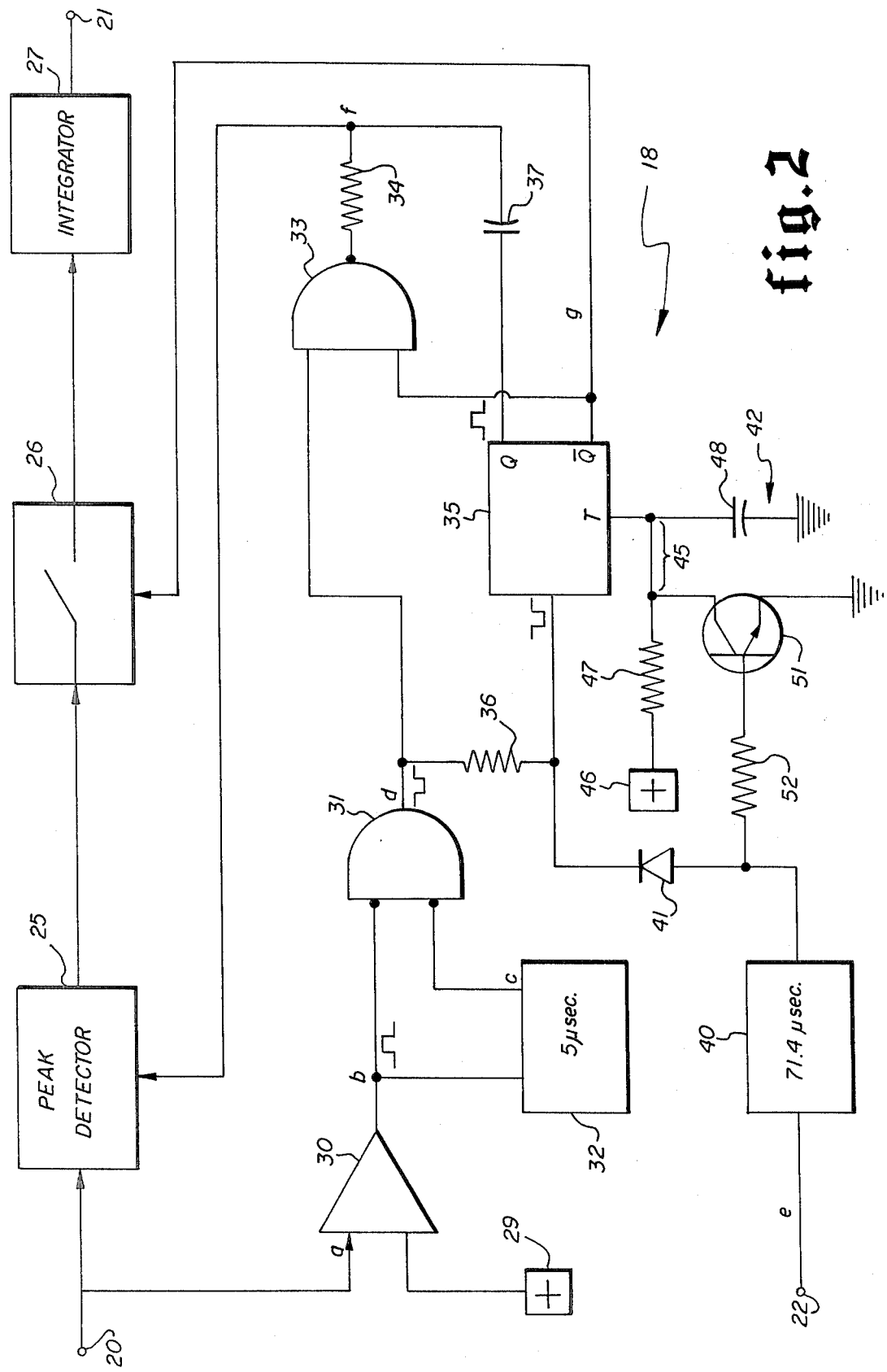
FIG. 2 is a schematic diagram of hematocrit measuring circuitry represented in block diagrammatic form in FIG. 1.

FIG. 2 is a schematic representation of the hematocrit computer 18 of FIG. 1. The same reference numerals are used to denote elements corresponding to those shown in FIG. 1. Waveforms and letters are noted at output terminals of certain components for purposes of description in connection with the discussion of FIGS. 3 and 4 below. The input terminal 20 of the hematocrit computer circuit 18 is connected to a peak detector 25. The peak detector 25 acts as a sample and hold circuit for holding the peak of each incoming sensor pulse above the threshold level. A controlled switching means 26 is connected between the peak detector 25 and accumulation means in the form of an integrator 27. The controlled switching means is controllable to increment the level in the accumulation means, i.e. to integrate an analog level indicative of the peak of each sensor pulse into the integrator 27. The integrator 27 accumulates the analog increments to provide a total analog level indicative of hematocrit for a sample 3. Further details of the operation and construction of the peak detector 25, controlled switching means 26 and integrator 27 are found in the above-cited U.S. Pat. No. 4,068,169 to Angel and Bachenheimer. The peak detector 25 is normally disabled, but is enabled in response to a sensor pulse exceeding the threshold level.

To provide this operation, another threshold detector, a threshold comparator 30 is provided comprising an operational amplifier having a first input connected to the input terminal 20 and a second input connected to a source 29 of threshold potential. Potential levels of inputs to the comparator 30 are selected such that a logic "one" is provided at the output thereof when a sensor pulse crosses the threshold level and so that a logic "zero" is provided when no sensor pulse or noise below the threshold level is present at the input to the operational amplifier 30. If desired, the threshold comparator 30 may also comprise the threshold comparator 7 (FIG. 1). The output of the comparator 30 is connected to one input of a NOR gate 31 and also to the input of a one shot multivibrator 32 connected in a non-retriggerable mode having its output connected to a second input of the NOR gate 31. The one shot multivibrator 32 is triggered on a positive-going transition; i.e. it is triggered in response to the presence of a sensor pulse exceeding the threshold level. The output of the NOR gate 31 will change state upon initiation of a sensor pulse and will remain in the changed state during the output period of the one shot multivibrator 32 and/or when a logic "one" is at the output of the comparator 30. When both of these inputs are again "zero", the output of the NOR gate 31 changes state again. In the preferred embodiment, based upon the expected range of cell sizes and the rate of aspiration of sample 3 into the probe 1 (FIG. 1), it is contemplated that the nominal sensor pulse will have a duration of 30 microseconds. The one shot multivibrator 32 is selected to provide an output having a duration of five microseconds. The output of the NOR gate 31 is utilized to determine a first period in which the peak detector 25 will be enabled to respond to sensor pulses.

The output of the NOR gate 31 is connected to a NAND gate 33, and is also coupled by a resistor 36 to an input of a one shot multivibrator 35 connected in the non-retriggerable mode. In accordance with the present invention as further described below, when no coincidence correction pulse is applied, the one shot multivibrator 35 will provide an output of a first and shorter time period. When a coincidence correction pulse is applied, the output of the one shot multivibrator 35 will provide an output having a duration of a second and longer time period. The one shot multivibrator has a non-inverted, or Q, output coupled by a capacitor 37 to the input of the peak detector 25. The resistor 34 and capacitor 37 form an RC circuit for permitting the peak detector 25 to respond to a second sensor pulse of a different size occurring within five microseconds after a first pulse, as explained in the above-cited U.S. Pat. No. 4,068,169 to Angel and Bachenheimer. The inverted, or Q̄, is connected to a second input of the NAND gate 33 and also to a control terminal of the controlled switching means 26. When the one shot multivibrator 35 is triggered, the Q output closes the controlled switching means 26 for incrementing the analog level in the integrator 27.

Further circuitry is provided to alter the time period of the output of the one shot multivibrator 35 from one preselected duration to another in accordance with the presence or absence of a coincidence correction pulse applied at the input terminal 22 of the hematocrit computer 18. It is this time period that defines the duration for which the integrator 27 is incremented at the level held by the peak detector 25. A shorter time period provides for incrementing in accordance with the level of the sensor pulse. A longer time period provides for additionally incrementing the level in the integrator 27 in response to production of a coincidence correction pulse.

A one shot multivibrator 40 is provided having an input connected to the input terminal 22 and having an output coupled to the input of the one shot multivibrator 35 by a diode 41 connected in a direction to pass the polarity of the output of the one shot multivibrator 40. The diode 41 blocks outputs from the NOR gate 31. The output of the one shot multivibrator 40 is also connected to a timing circuit 42 which is a RC circuit determining the period of the output of the one shot multivibrator 35. The one shot multivibrator 35 is of a well-known form in which the outputs thereof change state until a predetermined level at a threshold input terminal, denoted T in FIG. 2, is reached. The threshold level is provided by charging the RC circuit. An example of such a component is the well-known RCA 4528 integrated circuit. The threshold terminal T of the one shot multivibrator 35 is connected to a terminal 45 of the timing circuit 42. A source of charging potential 46 is connected to a first terminal of a resistor 47 having a second terminal connected to the terminal 45. A capacitor 48 is connected between the terminal 45 and ground. The resistor 47 and capacitor 48 form the RC circuit determining the time constant for charging to the level to determine the output period of the one shot multivibrator 35. Once an input is received at the multivibrator 35, the Q output thereof remains positive until the predetermined level at the T terminal is reached. In the preferred embodiment, the values of the resistor 47 and capacitor 48 are selected so that this time constant is 3.4 microseconds.

To provide for a selectable time period that will elapse until the preselected threshold level is provided, a controlled switching means is provided in the form of a transistor 51 having its emitter-collector circuit connected across the capacitor 48. The base of the transistor 51 is coupled by a resistor 52 to the output of the one shot multivibrator 40. Thus when a coincidence pulse is provided at the input terminal 22, the one shot multivibrator 40 provides an output having a logic level of one for a period of 71.4 microseconds. This output saturates the transistor 51 so that the capacitor 48 cannot charge. Thus the 3.4 microsecond period defined by the time constant of the timing circuit 42 cannot begin until the 71.4 microsecond period of the output of the one shot multivibrator 40 ends. In this manner, the controlled switching means 26 is held closed for a longer time to further increment the integrator 27 and compensate for coincidence.

The ratio of the output period of the one shot multivibrator 40 to that of the one shot multivibrator 35 represents the weighting of a coincidence correction pulse compared to that for a sensor pulse. This ratio is selected in accordance with an empirically determined degree of coincidence correction necessary and in accordance with the value of the divisor embodied in the divider 9 (FIG. 1). If desired further circuitry could be provided in accordance with the above teachings and the above-cited U.S. Pat. No. 4,042,808 to Hennessy et al to provide for selection of one of a number of different time periods for altering the weighting of a coincidence correction pulse depending on the level of red blood cell count.

Operation of the circuit is described with respect to FIGS. 3 and 4, which are waveform charts respectively illustrative of the cases in which no coincidence correction pulse is applied and in which a coincidence correction pulse is applied at the terminal 22 of the hematocrit computer circuit 18. FIGS. 3a and 4a represent the sensor pulse input to the threshold comparator 30; FIGS. 3b and 4b illustrate the output of the threshold comparator 30; FIGS. 3c and 4c represent the output of the one shot multivibrator 42; FIGS. 3d and 4d are representations of the output of the NOR gate 31; coincidence correction pulses are illustrated in FIGS. 3e and 4e; the enabling signal to the peak detector 25 is seen in FIGS. 3f and 4f; and FIGS. 3g and 4g indicate the state of the Q output of the one shot multivibrator 35. The abscissa in each figure is time, and the ordinates are in arbitrary units.

Operation in the case in which no coincidence correction pulse is produced is explained with respect to FIGS. 2 and 3. As seen in FIG. 3a, a sensor pulse is represented. When the value of the sensor pulse crosses the preselected threshold level (shown as a dotted line in FIG. 3a), the output of the threshold comparator 30 changes from a logic "zero" level to a "one" level (FIG. 3b). In the present example, the sensor pulse is a nominal sensor pulse having a duration of 30 microseconds above the threshold level. This output is supplied to the first input of the NOR gate 31 and to the input of the one shot multivibrator 32, which produces the 5 microsecond duration output illustrated in FIG. 3c. The NOR gate 31 will provide a "zero" logic value output when either input thereto is at a "one" level. Therefore, the NOR gate 31 produces the output illustrated in FIG. 3d having a duration equal to the longer of the sensor pulse or the five microsecond output from the one shot multivibrator 32, which is provided to insure a minimum length of five microseconds for the output of the NOR gate 31 in the event that a sensor pulse shorter than five microseconds is measured. This output (FIG. 3d) is coupled to the NAND gate 33 to cause it to produce an output (FIG. 3f) for enabling the peak detector 25 and respond to a sensor pulse.

The following operation provides for closing the switch 26 to increment the integrator 27 after the peak detector 25 measures and holds a peak level. The output of the NOR gate 31 seen in FIG. 3d, is applied to the triggering input of the one shot multivibrator 35. The production of the 3.4 microsecond output pulse is triggered when on the positive going transition when the output of the NOR gate 31 returns to the "one" level. The Q output goes negative to close the controlled switching means 26 (FIG. 3g).

Operation is illustrated in FIG. 4 when a coincidence correction pulse is provided at the input terminal 22 of the hematocrit computer circuit 18. The response to an incoming sensor pulse is the same as in the first case, and this is illustrated in FIGS. 4a through 4d. However, as seen in FIG. 4e, when an incoming coincidence correction pulse, represented by a negative going transition, occurs, the 71.4 microsecond one shot multivibrator 40 is triggered to provide an output for a period of 71.4 microseconds. This output is also a negative going transition, having a logic level of "zero". This zero level provides an input to saturate the transistor 51 so that the terminal 45 of the timing circuit 42 is connected to ground potential and the timing circuit 42 cannot charge. Consequently, the period of the output of the multivibrator 35 is equal to 71.4 seconds plus the 3.4 microseconds which will elapse after the transistor 51 is turned off. In this manner, the controlled switching means 26 is closed for an additional period of time to further increment the integrator 27 for a longer period of time at an analog level equal to the last sensor pulse peak sensed by the peak detector 25. The sensor pulse peaks will vary in level. However, there will be a large enough statistical sample of sensor pulse peaks so that over one counting period, the overall additional accumulation of the integrator 27 will represent the sizes of all blood cells not counted due to coincidence. In this manner, coincidence correction is achieved.

The specification has been written with a view toward enabling those skilled in the art to make many modifications to provide a hematocrit measuring circuitry with coincidence correction constructed in accordance with the present invention.

What is claimed as new and desired to be secured by Letters Patent of the United States is:

1. In a hematocrit measurement apparatus comprising peak detector means for responding to sensor pulses and means for incrementing an accumulation means in accordance with pulse levels sensed by said peak detecting means, the improvement of hematocrit coincidence correction means comprising first means coupled for receiving inputs indicative of the production of coincidence correction pulses insertable into a red blood cell pulse train to correct red blood cell count for coincidence and second means coupled said first means and responsive to an input from said first means for providing an output to control incrementing of said accumulation means by an amount in addition to the incrementing thereof in response to a sensor pulse.

2. The apparatus according to claim 1 comprising first timing means connected to controlled switching means coupled between said peak detector and said accumulation means for closing said controlled switching means for a first preselected period of time in response to a sensor pulse and second timing means for establishing a second and longer preselected time period for closing said controlled switching means for said second time period in response to a coincidence correction pulse insertable into a red blood cell pulse train to correct red blood cell count for coincidence.

3. In a hematology measurement apparatus comprising hematocrit measurement means including means for incrementing a value held by accumulation means responsive to measurement of size of sensed blood cells and further comprising means for generating red blood cell count coincidence correction pulses, the improvement comprising timing means for providing an output of a first or second state and connected for disabling incrementing of the value in said accumulation means when the output of said timing means is of a first state and for enabling incrementing of the value in said accumulation means when the output of said timing means is of a second state, said timing means being connected to change state for an output period in response to occurrence of a sensor pulse, time period determining means connected to said timing means having an output connected for selecting one of a plurality of preselected values of the output period in dependence upon the value of the output of said time period determining means, said time period determining means having an input connected for sensing the occurrence of a red blood cell count coincidence correction pulse and for providing an output for selecting a first and shorter time period in the absence of a coincidence correction pulse and providing an output for selecting another and longer time period in response to a red blood cell count coincidence correction pulse immediately following a sensor pulse.

4. The improvement according to claim 3 wherein said timing means comprises a first one shot multivibrator connected in the non-retriggerable mode.

5. The improvement according to claim 4 wherein said first one shot multivibrator comprises a threshold terminal for terminating the output period when the potential thereat reaches a preselected level and wherein said time period determining means comprises an RC circuit connected to said threshold terminal and having a period defining the first time period, said RC circuit being connected to commence charging in response to an input to said first one shot multivibrator indicative of a sensor pulse.

6. The improvement according to claim 5 wherein said time period determining means further comprises controlled switching means connected for selectively disabling charging of said RC circuit and a second one shot multivibrator having an output connected to a control terminal of said switching means, said second one shot multivibrator having an input connected to a source of pulses indicative of the production of coincidence correction pulses, and being triggerable to provide an output for disabling said RC circuit for a second preselected time period in response to occurrence of a coincidence correction pulse, whereby the output period is extended and the said another and longer time period is provided.

7. In a method for measuring hematocrit comprising the steps of measuring a peak indicative of the size of a sensed blood cell and incrementing accumulation means in accordance therewith, the improvement of coincidence correction comprising the step of detecting coincidence correction pulses insertable into a red blood cell pulse train to correct red blood cell count for coincidence and controlling further incrementing of said accumulation means in response to coincidence correction pulses.

8. In a hematology measurement method comprising the steps of measuring hematocrit by incrementing a value held by accumulation means in response to measurement of size of sensed blood cells and further comprising the step of generating red blood cell count coincidence correction pulses, the improvement of providing timing means for operation to increment for an output period said accumulation means in response to occurrence of a sensor pulse, sensing the presence or absence of a red blood cell count coincidence correction pulse following a sensor pulse, and selecting the duration of the output period from one of a plurality of preselected periods in correspondence to the presence or absence of the coincidence correction pulse.

9. The improvement according to claim 8 wherein the step of selecting the duration comprises selecting a first and shorter duration in response to the absence of the coincidence correction pulse and selecting a second and longer period in response to the presence thereof.

10. The improvement according to claim 9 wherein the step of providing timing means comprises providing a one shot multivibrator and a time constant charging circuit thereto for determining the output period thereof and wherein the step of selecting the first duration period comprises allowing the charging circuit to charge in a time period equal to the time constant thereof and wherein the step of selecting the second duration period comprises disabling the charging circuit from charging for a preselected period prior to allowing the time constant circuit to charge.

11. The improvement according to claim 3 wherein said timing means is connected to change state for an output period in response to the end of a sensor pulse.

12. The improvement according to claim 5 wherein said RC circuit is connected to commence charging in response to an input to said first one shot multivibrator indicative of the end of a sensor pulse.

* * * * *